United States Patent
Beeckler et al.

(10) Patent No.: US 12,076,165 B2
(45) Date of Patent: Sep. 3, 2024

(54) ACCURATE BASKET CATHETER TRACKING

(71) Applicant: Biosense Webster (Israel) Ltd., Yokneam (IL)

(72) Inventors: Christopher Thomas Beeckler, Brea, CA (US); Vadim Gliner, Haifa (IL); Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

(21) Appl. No.: 18/450,529

(22) Filed: Aug. 16, 2023

(65) Prior Publication Data

US 2023/0397884 A1 Dec. 14, 2023

Related U.S. Application Data

(62) Division of application No. 16/854,538, filed on Apr. 21, 2020, now Pat. No. 11,759,150.

(Continued)

(51) Int. Cl.
*A61B 5/00* (2006.01)
*A61B 5/06* (2006.01)

(52) U.S. Cl.
CPC .......... *A61B 5/6858* (2013.01); *A61B 5/062* (2013.01); *A61B 5/065* (2013.01)

(58) Field of Classification Search
CPC ... A61B 2304/2051; A61B 5/062; A61B 5/65; A61B 5/6858
See application file for complete search history.

(56) References Cited

U.S. PATENT DOCUMENTS

| 5,391,199 A | 2/1995 | Ben-Haim |
| 6,239,724 B1 | 5/2001 | Doron et al. |

(Continued)

FOREIGN PATENT DOCUMENTS

| EP | 1126787 B1 | 6/2008 |
| EP | 3178384 A1 | 6/2017 |

(Continued)

OTHER PUBLICATIONS

Extended European Search Report dated Dec. 18, 2020, from corresponding European Application No. 20192792.8.

(Continued)

*Primary Examiner* — Rajeev P Siripurapu
(74) *Attorney, Agent, or Firm* — Troutman Pepper Hamilton Sanders LLP

(57) ABSTRACT

In one embodiment, a system includes a catheter including an insertion tube and a first position sensor, a pusher including a second position sensor, and an expandable assembly including flexible strips disposed circumferentially around a distal portion of the pusher, with first ends of the strips connected to the distal end of the insertion tube and second ends of the strips connected to the distal portion of the pusher, the flexible strips bowing radially outward when the pusher is retracted, processing circuitry to receive a respective position signal from the first and second position sensors, compute location and orientation coordinates for the position sensors subject to a constraint that the position sensors are coaxial and have a same orientation, compute a distance between the computed location coordinates of the position sensors, and find position coordinates of the flexible strips responsively to at least the computed distance.

20 Claims, 6 Drawing Sheets

Related U.S. Application Data

(60) Provisional application No. 62/892,487, filed on Aug. 27, 2019.

(56) References Cited

U.S. PATENT DOCUMENTS

| | | |
|---|---|---|
| 6,332,089 B1 | 12/2001 | Acker et al. |
| 6,484,118 B1 | 11/2002 | Govari |
| 6,618,612 B1 | 9/2003 | Acker et al. |
| 6,625,563 B2 | 9/2003 | Kirsch et al. |
| 6,690,963 B2 | 2/2004 | Ben-Haim et al. |
| 2002/0065455 A1 | 5/2002 | Ben-Haim et al. |
| 2002/0198676 A1 | 12/2002 | Kirsch et al. |
| 2003/0120150 A1 | 6/2003 | Govari |
| 2004/0068178 A1 | 4/2004 | Govari |
| 2006/0009689 A1 | 1/2006 | Fuimaono et al. |
| 2006/0009690 A1 | 1/2006 | Fuimaono et al. |
| 2010/0030063 A1 | 2/2010 | Lee et al. |
| 2011/0282187 A1 | 11/2011 | Harlev et al. |
| 2011/0313414 A1 | 12/2011 | Liu et al. |
| 2012/0150022 A1 | 6/2012 | Bar-Tal et al. |
| 2015/0025365 A1 | 1/2015 | Esguerra Wilczynski et al. |
| 2015/0150472 A1 | 6/2015 | Harlev et al. |
| 2017/0181706 A1 | 6/2017 | Montag et al. |
| 2018/0042516 A1 | 2/2018 | Olson et al. |
| 2018/0160936 A1 | 6/2018 | Govari |

FOREIGN PATENT DOCUMENTS

| | | |
|---|---|---|
| EP | 3571989 A1 | 11/2019 |
| EP | 3682797 A2 | 7/2020 |
| JP | 2012125579 A | 7/2012 |
| JP | 2018511392 A | 4/2018 |
| JP | 2018094417 A | 6/2018 |
| WO | 1996005768 A1 | 2/1996 |

OTHER PUBLICATIONS

Search Report and English translation dated Apr. 12, 2024, from corresponding Japanese Application No. 2020-142376.

Notice of Reasons for Refusal and English translation dated Apr. 30, 2024, from corresponding Japanese Application No. 2020-142376.

ACCURATE BASKET CATHETER TRACKING

RELATED APPLICATION INFORMATION

This application is a divisional of prior filed U.S. patent application Ser. No. 16/854,538 filed on Apr. 21, 2020, which claims benefit of U.S. Provisional Patent Application No. 62/892,487 of Beeckler, et al. filed on Aug. 27, 2019, which prior application is hereby incorporated by reference as if set forth in full into this application.

FIELD OF THE INVENTION

The present invention relates to medical devices, and in particular to, tracking position of catheters.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,625,563, 6,690,963, 6,484,118, 6,239,724, 6,618,612 and 6,332,089, in PCT International Publication No. WO 1996/005768, and in U.S. Patent Application Publications Nos. 2003/0120150 and 2004/0068178, whose disclosures are all incorporated herein by reference. Locations may also be tracked using impedance or current based systems.

European Patent Publication 3,178,384 of Hoitink, et al., describes a catheter having a dual node multiray electrode assembly at the distal end of the catheter body. The dual node multiray electrode assembly includes a proximal multiray array with a plurality of spines connected at one end, each spine having at least one ablation electrode, and a distal node. The dual node multiray electrode assembly may have an expanded configuration and a collapsed configuration wherein the spines are arranged generally along a longitudinal axis of the catheter body. The distal node may be configured to be deployed within a vessel and the proximal multiray array may be configured to engage tissue forming an ostium of the vessel with the ablation electrodes. In some embodiments, the relative distance between the proximal multiray array and the distal node is adjustable.

US Patent Publication 2017/0181706 of Montag, et al., describes catheterization of the heart being carried out using a framework formed by a plurality of electrically conducting wire loops. The wire loops are modeled as polygons, each subdivided into a plurality of triangles. The wire loops are exposed to magnetic fluxes at respective frequencies, and signals read from the loops. Theoretical magnetic fluxes in the polygons are computed as sums of theoretical magnetic fluxes in the triangles thereof. The location and orientation of the framework in the heart is determined by relating the computed theoretical magnetic fluxes to the signals.

US Patent Publication 2015/0025365 of Esguerra, et al., describes a catheter having single axis sensors mounted directly along a portion of the catheter whose position/location is of interest. The magnetic based, single axis sensors are on a linear or nonlinear single axis sensor (SAS) assembly. The catheter includes a catheter body and a distal 2D or 3D configuration provided by a support member on which at least one, if not at least three single axis sensors, are mounted serially along a length of the support member. The magnetic-based sensor assembly may include at least one coil member wrapped on the support member, wherein the coil member is connected via a joint region to a respective cable member adapted to transmit a signal providing location information from the coil member to a mapping and localization system. The joint region provides strain relief adaptations to the at least one coil member and the respective cable member from detaching.

US Patent Publication 2015/0150472 of Harley, et al., describes a non-contact cardiac mapping method that includes: (i) inserting a catheter into a heart cavity having an endocardium surface, the catheter including multiple, spatially distributed electrodes; (ii) measuring signals at the catheter electrodes in response to electrical activity in the heart cavity with the catheter spaced from the endocardium surface; and (iii) determining physiological information at multiple locations of the endocardium surface based on the measured signals and positions of the electrodes with respect to the endocardium surface.

US Patent Publication 2006/0009689 of Fuimaono, et al., describes an improved basket catheter is provided that is particularly useful for mapping the heart. The catheter comprises an elongated catheter body having proximal and distal ends and at least one lumen therethrough. A basket-shaped electrode assembly is mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

US Patent Publication 2002/0198676 of Kirsch, et al., describes a system for determining the position, orientation and system gain factor of a probe includes a plurality of magnetic field sources and at least one magnetic field sensor, such that a combination of a magnetic field sensor and a magnetic field source generates a unique measured magnetic field value. The system includes a probe whose gain, position, and orientation affect these unique measured magnetic field values. A processor is configured to receive and iteratively process these unique measured magnetic field values to determine a system gain factor indicative of the gain of the probe and a plurality of location factors indicative of the position and orientation of the probe. The number of unique measured magnetic field values generated must be at least equal to the sum of the number of gain and location factors calculated.

The background section of Kirsch, et al., mentions that determining a probe's location and orientation from magnetic field measurements is not straight forward because the measured magnetic fields are nonlinear functions of the location and orientation. To determine the probe's location and orientation from the measured magnetic field values, the probes location and orientation are first presumed or "guessed" to be at a predicted location and orientation. An iterative process is used to compare values of the magnetic field at the guessed probe location and orientation with the measured field values. If the magnetic field values at a guessed location and orientation are close to the measured values, the guessed location and orientation are presumed to accurately represent the actual location and orientation of the probe. The iterative process uses a physical model for the probe's environment. The physical model specifies the location and orientation of each field source. From the specified locations and orientations, laws of electrodynamics determine the field values.

SUMMARY

There is provided in accordance with an embodiment of the present disclosure, a system including a catheter configured to be inserted into a body-part of a living subject, and including an insertion tube including a distal end, and a first coil-based position sensor disposed at the distal end, a pusher including a second coil-based position sensor disposed thereon and a distal portion, and being configured to be advanced and retracted through the insertion tube, and an expandable assembly including a plurality of flexible strips disposed circumferentially around the distal portion of the pusher, with first ends of the strips connected to the distal end of the insertion tube and second ends of the strips connected to the distal portion of the pusher, the flexible strips being configured to bow radially outward when the pusher is retracted, at least one magnetic field radiator configured to transmit alternating magnetic fields into a region where the body-part is located, the first and second position sensors being configured to output respective first and second position signals in response to the transmitted alternating magnetic fields, and processing circuitry configured to receive the first and second position signals from the first and second position sensors, compute location and orientation coordinates for the first and second position sensors using a position computation in which the location and orientation coordinates of each of the position sensors are interdependently computed in an iterative manner responsively to the respective received position signals, and subject to a constraint that the first and second position sensors are coaxial, compute a distance between the computed location coordinates of the first position sensor and the computed location coordinates of the second position sensor, and estimate respective positions of the flexible strips responsively to at least the computed distance.

Further in accordance with an embodiment of the present disclosure, the system includes a display, wherein the processing circuitry is configured to compute a roll of the expandable assembly responsively to the position signal from at least one of the first or second position sensors, and render to the display a representation of at least a part of the catheter and the body-part responsively to the estimated respective positions of the flexible strips.

Still further in accordance with an embodiment of the present disclosure the processing circuitry is configured to compute the location and orientation coordinates for one sensor of the first and second position sensors using the position computation, and compute the location coordinates for another sensor of the first and second position sensors subject to a constraint that the computed orientation coordinates for the other sensor will be equal to the computed orientation coordinates of the one sensor within a given tolerance.

Additionally, in accordance with an embodiment of the present disclosure the processing circuitry is configured to compute initial location and initial orientation coordinates for the first and second position sensors using the position computation, compute an average of the initial orientation coordinates of the first and second position sensors, and compute the location and orientation coordinates for the first and second position sensors using the position computation subject to a constraint that the orientation coordinates for the first and second position sensors will be equal to the computed average of the initial orientation coordinates with a given tolerance.

Moreover, in accordance with an embodiment of the present disclosure the processing circuitry is configured to compute the location and orientation coordinates for the first and second position sensors subject to a constraint that the computed orientation coordinates for the first and second position sensors will be equal within a given tolerance.

There is also provided in accordance with another embodiment of the present disclosure, a system including a catheter configured to be inserted into a body-part of a living subject, and including an insertion tube including a distal end, and a first coil-based position sensor disposed at the distal end, a pusher including a second coil-based position sensor disposed thereon and a distal portion, and being configured to be advanced and retracted through the insertion tube, and an expandable assembly including a plurality of flexible strips disposed circumferentially around the distal portion of the pusher, with first ends of the strips connected to the distal end of the insertion tube and second ends of the strips connected to the distal portion of the pusher, the flexible strips being configured to bow radially outward when the pusher is retracted, at least one magnetic field radiator configured to transmit alternating magnetic fields into a region where the body-part is located, the first and second position sensors being configured to output respective first and second position signals in response to the transmitted alternating magnetic fields, and processing circuitry configured to receive the first and second position signals from the first and second position sensors, compute a distance and a relative orientation angle between the first and second position sensors responsively to the received position signals, and estimate respective positions of the flexible strips responsively to at least the computed distance and relative orientation angle, while accounting for a distortion of one or more of the flexible strips from a symmetrical disposition when the relative orientation angle has a value greater than zero.

Further in accordance with an embodiment of the present disclosure, the system includes a display, wherein the processing circuitry is configured to compute a roll of the expandable assembly responsively to the position signal from at least one of the first or second position sensors, and render to the display a representation of at least a part of the catheter and the body-part responsively to the estimated respective positions of the flexible strips.

There is also provided in accordance with still another embodiment of the present disclosure, a method, including inserting a catheter into a body-part of a living subject, the catheter including an insertion tube, a first coil-based position sensor disposed at a distal end of the insertion tube, a pusher including a second coil-based position sensor disposed thereon, an expandable assembly including flexible strips disposed circumferentially around a distal portion of the pusher, with first ends of the strips connected to the distal end of the insertion tube and second ends of the strips connected to the distal portion of the pusher, retracting the pusher causing the flexible strips to bow radially outward, transmitting alternating magnetic fields into a region where the body-part is located, outputting by the first and second position sensors respective first and second position signals in response to the transmitted alternating magnetic fields, receiving the first and second position signals from the first and second position sensors, computing location and orientation coordinates for the first and second position sensors using a position computation in which the location and orientation coordinates of each of the position sensors are interdependently computed in an iterative manner responsively to the respective received position signals, and subject to a constraint that the first and second position sensors are coaxial, computing a distance between the computed location coordinates of the first position sensor and the computed location coordinates of the second position sensor, and estimating respective positions of the flexible strips responsively to at least the computed distance.

Still further in accordance with an embodiment of the present disclosure, the method includes computing a roll of the expandable assembly responsively to the position signal from at least one of the first or second position sensors, and rendering to a display a representation of at least a part of the catheter and the body-part responsively to the estimated respective positions of the flexible strips.

Additionally, in accordance with an embodiment of the present disclosure, the method includes computing the location and orientation coordinates for one sensor of the first and second position sensors using the position computation, and computing the location coordinates for another sensor of the first and second position sensors subject to a constraint that the computed orientation coordinates for the other sensor will be equal to the computed orientation coordinates of the one sensor within a given tolerance.

Moreover, in accordance with an embodiment of the present disclosure, the method includes computing initial location and initial orientation coordinates for the first and second position sensors using the position computation, computing an average of the initial orientation coordinates of the first and second position sensors, and computing the location and orientation coordinates for the first and second position sensors using the position computation subject to a constraint that the orientation coordinates for the first and second position sensors will be equal to the computed average of the initial orientation coordinates with a given tolerance.

Further in accordance with an embodiment of the present disclosure, the method includes computing the location and orientation coordinates for the first and second position sensors subject to a constraint that the computed orientation coordinates for the first and second position sensors will be equal within a given tolerance.

There is also provided in accordance with still another embodiment of the present disclosure, a method, including inserting a catheter into a body-part of a living subject, the catheter including an insertion tube, a first coil-based position sensor disposed at a distal end of the insertion tube, a pusher including a second coil-based position sensor disposed thereon, an expandable assembly including flexible strips disposed circumferentially around a distal portion of the pusher, with first ends of the strips connected to the distal end of the insertion tube and second ends of the strips connected to the distal portion of the pusher, retracting the pusher causing the flexible strips to bow radially outward, transmitting alternating magnetic fields into a region where the body-part is located, outputting by the first and second position sensors respective first and second position signals in response to the transmitted alternating magnetic fields, receiving the first and second position signals from the first and second position sensors, computing a distance and a relative orientation angle between the first and second position sensors responsively to the received position signals, and estimating respective positions of the flexible strips responsively to at least the computed distance and relative orientation angle, while accounting for a distortion of one or more of the flexible strips from a symmetrical disposition when the relative orientation angle has a value greater than zero.

Still further in accordance with an embodiment of the present disclosure, the method includes computing a roll of the expandable assembly responsively to the position signal from at least one of the first or second position sensors, and rendering to the display a representation of at least a part of the catheter and the body-part responsively to the estimated respective positions of the flexible strips.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
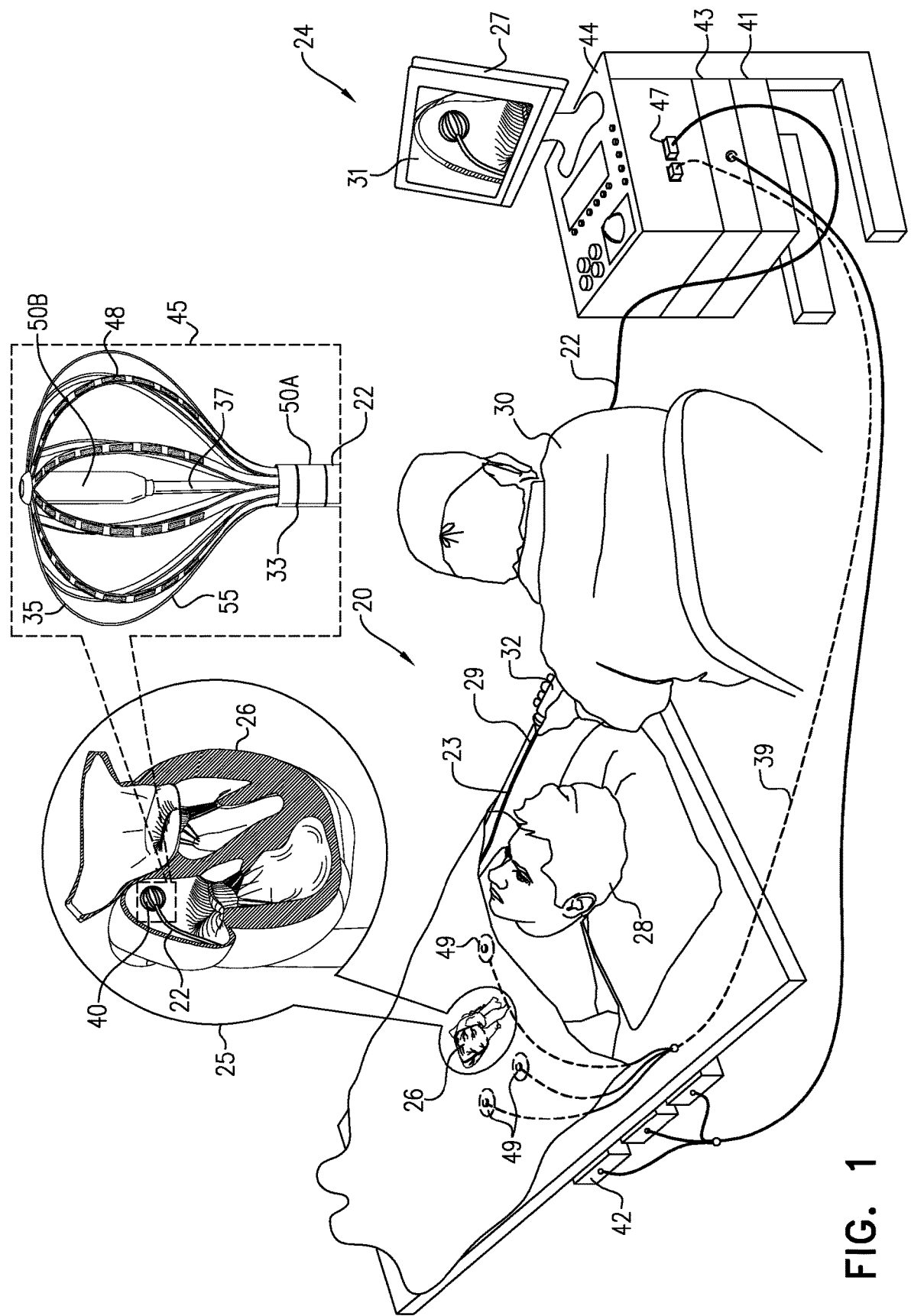
FIG. 1 is a schematic, pictorial illustration of a system for electro-anatomical mapping comprising a catheter, in accordance with an embodiment of the present invention.

The Carto®3 system (produced by Biosense Webster, Inc., Irvine, California) applies Advanced Catheter Location (ACL) hybrid position-tracking technology. In ACL technology, distribution of measured currents associated with probe electrodes on a catheter are correlated with a current-to-position matrix (CPM), which maps the current distribution to a position of the catheter that was previously acquired from magnetic location-calibrated position signals. The ACL technology enables locating and visualizing a catheter (even a catheter which does not have a magnetic field sensor), but only in the volume(s) where the CPM has been computed, using a catheter with a magnetic sensor. A prerequisite for building the CPM is to insert a magnetic-field sensor-equipped catheter into a body and move the catheter in a volume of the body, in order to compute the CPM for that volume.

ACL technology may be used to track a basket catheter which has electrodes on the basket. However, ACL technology, which measures currents or impedances, may not provide high enough accuracy in some situations.

Embodiments of the present invention compute position coordinates of a basket catheter using magnetic-based tracking technology based on two coil-based position sensors to provide an accurate computation of the position of the basket and its electrodes. At least one magnetic field radiator transmits alternating magnetic fields into a region where a body-part is located and the coil-based position sensors output respective position signals in response to the transmitted alternating magnetic fields so that the respective position signals read from the coils provide information about the position of the coils.

In some embodiments, the catheter includes an insertion tube including a lumen and a first coil-based position sensor disposed at a distal end of the insertion tube. The catheter also includes a pusher including a second coil-based position sensor disposed thereon. The pusher is advanced and retracted through the lumen, as will be explained in more detail below. The position sensors may be selected from single, dual, or triple axis sensors, as will be described with reference to disclosed embodiments.

The catheter also includes an expandable assembly (e.g., basket assembly) comprising flexible strips disposed circumferentially around the distal portion of the pusher, with first ends of the strips connected to the distal end of the insertion tube and second ends of the strips connected to the distal end of the pusher. The flexible strips bow radially outward when the pusher is retracted and flatten when the pusher is pushed in the direction of the distal end of the catheter. Each of the flexible strips includes multiple electrodes disposed thereon.

Although the strips are flexible, the strips are sturdy enough so that a computed inter-coil distance between the first coil-based position sensor and the second coil-based position sensor should provide an accurate estimate of the shape of the flexible strips. However, the difference between the inter-coil distance when the basket is fully deployed and when the basket is fully closed may be around 4 mm for some baskets and around 10 mm for other baskets, depending on the dimensions of the basket. Additionally, the resolution of the magnetic-based tracking technology may be around 1 mm Therefore, the inter-coil distance computed using the magnetic-based tracking technology may not be accurate enough to accurately predict the shape of the flexible strips.

Some embodiments use a novel position computation to more accurately compute the inter-coil distance based on the assumption that the first coil-based position sensor and the second coil-based position sensor are coaxial. In other words, one of the sensors includes a coil which is coaxial with a coil of the other sensor and with the axis of the insertion tube of the catheter. The novel position computation may improve the accuracy of position measurements from around 1 mm to around 0.1 mm, by way of example only.

The system includes processing circuitry which receives the respective position signals from the first and second position sensors. The processing circuitry computes location and orientation coordinates for the first and second position sensors using a position computation in which the location and orientation coordinates of each of the position sensors are interdependently computed in an iterative manner responsively to the respective position signals. The position computation is interdependent such that the location coordinates computed for one of the sensors based on the signal(s) received from that sensor is dependent upon the orientation coordinates computed for that sensor, and vice-versa. Similarly, an error (e.g., due to noise or any other factor) in computing the location coordinates leads to an inaccuracy in computing orientation, and vice-versa.

Any suitable iterative position computation may be used. For example, US Patent Publication 2002/0198676 of Kirsch, et al., which is herein incorporated by reference, describes an iterative position computation in its background section and some enhancements in the detailed description. The background section of Kirsch, et al., mentions that determining a probes location and orientation from magnetic field measurements is not straight forward because the measured magnetic fields are nonlinear functions of the location and orientation. To determine the probes location and orientation from the measured magnetic field values, the probes location and orientation are first presumed or "guessed" to be at a predicted location and orientation. An iterative process is used to compare values of the magnetic field at the guessed probe location and orientation with the measured field values. If the magnetic field values at a guessed location and orientation are close to the measured values, the guessed location and orientation are presumed to accurately represent the actual location and orientation of the probe. The position computations described in the Kirsch, et al., publication may provide suitable iterative position computations, mutatis mutandis, for use in embodiments of the present disclosure. For example, the iterative position computations described in Kirsch, et al., may be subject to a constraint with respect to the orientation as described below.

European Patent Publication 1,126,787 of Golden, et al., which is herein incorporated by reference, describes an iterative position computation which may provide a suitable iterative position computation, mutatis mutandis, for use in embodiments of the present disclosure.

Based on the interdependent and iterative nature of the computation, improvement in accuracy of location measurements may be achieved by subjecting the position computation to a constraint that the first and second position sensors are coaxial based on the known geometry of the catheter and therefore both sensors have a same orientation which is used in the position computation of both sensors.

In some embodiments, the processing circuitry computes the location and orientation coordinates for the first and second position sensors subject to a constraint that the computed orientation coordinates for the first and second position sensors will be equal to within a given tolerance. Forcing the orientation coordinates to be equal generally results in more accurately computed location coordinates.

In other embodiments, the processing circuitry computes the location and orientation coordinates for one of the sensors (sensor A) using the position computation and then computes the location coordinates for the other sensor (sensor B) subject to a constraint that the computed orientation coordinates for sensor B will be equal to the already computed orientation coordinates of sensor A to within a given tolerance, such as plus or minus 2 degrees.

In yet other embodiments, the processing circuitry computes initial location and initial orientation coordinates for both sensors using the position computation based on the signals received from the sensors and then computes an average of the initial orientation coordinates of both sensors.

The processing circuitry then computes the location and orientation coordinates for each sensor using the position computation based on the signals received from the respective sensors and subject to a constraint that the final computed orientation coordinates for each sensor will be equal to the computed average of the initial orientation coordinates to within a given tolerance, such as plus or minus 2 degrees.

The computed location coordinates of the first and second sensor may be used to compute a distance between the first and second position sensor.

Based on a knowledge of the mechanical properties of the flexible strips and/or by performing pre-calibration to find which inter-coil distances correspond to which bowing of the flexible strips (at various distance between the sensors), respective positions of the flexible strips may be estimated responsively to computed distance as well as a roll of the basket which may be computed from signals of a dual-axis or triple-axis position sensor disposed on the catheter. The processing circuitry renders to a display a representation of at least a part of the catheter and the body-part responsively to the estimated respective positions of the flexible strips and the computed roll.

In some embodiments, improved distance measurements may be provided by one of the sensors being used as a local transmitter, and the other sensor as a local receiver. The transmitter may then transmit signals to the receiver in a different frequency than is used by the magnetic field radiator(s) described above. The locally transmitted and received signals may provide additional information regarding the locations of both sensors (such as the distance between the sensors according to the intensity of the received signal) and this may be used to increase the accuracy of the basket visualization.

In some embodiments, where the pusher and basket are flexible enough to be push to one side (for example, when pressed against tissue in the body-part) with respect to an axis of the insertion tube, the processing circuitry may compute a distance and a relative orientation angle between the first and second position sensors responsively to the received position signals. A non-zero relative orientation angle is then indicative that the expandable assembly (e.g., the basket) is deflected to a side with respect to an axis of the insertion tube, and that at least some of the flexible strips are distorted as compared to a shape of the flexible strips when the expandable assembly is centrally positioned around the axis of the insertion tube. Based on a knowledge of the mechanical properties of the flexible strips and/or by performing pre-calibration to find which relative orientation angle corresponds to which deformation of the flexible strips (at distance between the sensors), respective positions of the flexible strips (including the distorted flexible strips) may be estimated responsively to at least the computed distance and relative orientation angle while accounting for a distortion of one or more of the flexible strips from a symmetrical disposition when the relative orientation angle has a value greater than zero.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

Reference is now made to FIG. 1, which is a schematic, pictorial illustration of a catheter tracking system 20, in accordance with an embodiment of the present invention. The system 20 includes a catheter 40 configured to be inserted into a body part of a living subject (e.g., a patient 28). A physician 30 navigates the catheter 40 (for example, a basket catheter produced Biosense Webster, Inc. of Irvine, CA, USA), seen in detail in inset 45, to a target location in a heart 26 of the patient 28, by manipulating a deflectable segment of an insertion tube 22 of the catheter 40, using a manipulator 32 near a proximal end 29 of the insertion tube 22, and/or deflection from a sheath 23. In the pictured embodiment, physician 30 uses catheter 40 to perform electro-anatomical mapping of a cardiac chamber.

The insertion tube 22 includes a distal end 33 The catheter 40 includes an assembly 35 (e.g., a basket assembly) on which multiple electrodes 48 (only some labeled for the sake of simplicity) are disposed. The assembly 35 is disposed distally to the insertion tube 22 and may be connected to the insertion tube 22 via a coupling member of the insertion tube 22 at the distal end 33. The coupling member of the insertion tube 22 may formed as an integral part of the rest of the insertion tube 22 or as a separate element which connects with the rest of the insertion tube 22.

The assembly 35 further comprises multiple flexible strips 55 (only one labeled for the sake of simplicity), to each of which are coupled the electrodes 48. The assembly 35 may include any suitable number of electrodes 48. In some embodiments, the assembly 35 may include ten flexible strips 55 and 120 electrodes, with 12 electrodes disposed on each flexible strip 55.

The catheter 40 includes a pusher 37. The pusher 37 is typically a tube that is disposed in a lumen of the insertion tube 22 and spans from the proximal end 29 to the distal end 33 of the insertion tube 22. A distal end of the pusher 37 is connected to first ends of the flexible strips 55, typically via a coupling member of the pusher 37. The coupling member of the pusher 37 may formed as an integral part of the rest of the pusher 37 or as a separate element which connects with the rest of the pusher 37. The distal end of the insertion tube 22 is connected to second ends of the flexible strips 55, typically via the coupling member of the distal end 33. The pusher 37 is generally controlled via the manipulator 32 to deploy the assembly 35 and change an ellipticity of the assembly 35 according to the longitudinal displacement of the pusher 37 with respect to the insertion tube 22.

The actual basket assembly 35 structure may vary. For example, flexible strips 55 may be made of a printed circuit board (PCB), or of a shape-memory alloy.

Embodiments described herein refer mainly to a basket distal-end assembly 35, purely by way of example. In alternative embodiments, the disclosed techniques can be used with a catheter having a balloon-based distal-end assembly or of any other suitable type of distal-end assembly.

Catheter 40 is inserted in a folded configuration, through sheath 23, and only after the catheter 40 exits sheath 23 does catheter 40 regain its intended functional shape. By containing catheter 40 in a folded configuration, sheath 23 also serves to minimize vascular trauma on its way to the target location.

Catheter 40 may incorporate a magnetic sensor 50A, seen in inset 45, at the distal edge of insertion tube 22 (i.e., at the proximal edge of basket assembly 35). Typically, although not necessarily, sensor 50A is a Single-Axis Sensor (SAS). A second magnetic sensor 50B may be included at any suitable position on the pusher 37. Sensor 50B may be a Triple-Axis Sensor (TAS) or a Dual-Axis Sensor (DAS), or a SAS by way of example only, based for example on sizing considerations.

Magnetic sensors 50A and 50B and electrodes 48 are connected by wires running through insertion tube 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between sensors 50A and 50B. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in sensors 50A and 50B, which are indicative of position and/or direction. The generated signals are transmitted to console 24 and become corresponding electrical inputs to processing circuitry 41. The processing circuitry 41 uses the signals to calculate the elongation of the basket assembly 35, and to estimate basket ellipticity and elongation/retraction state from the calculated distance between sensors 50A and 50B, described in more detail below with reference to FIGS. 2-5.

The method of position and/or direction sensing using external magnetic fields and magnetic sensors, such as 50A and 50B, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processing circuitry 41, typically part of a general-purpose computer, is further connected via a suitable front end and interface circuits 44, to receive signals from surface-electrodes 49. Processing circuitry 41 is connected to surface-electrodes 49 by wires running through a cable 39 to the chest of patient 28.

The catheter 40 includes a connector 47 disposed at the proximal end 29 of the insertion tube 22 for coupling to the processing circuitry 41.

In an embodiment, processing circuitry 41 renders to a display 27, a representation 31 of at least a part of the catheter 40 and a body-part, from a scan (e.g., CT or MRI) of the body-part previously registered with the system 20, responsively to computed position coordinates of the insertion tube 22 and the flexible strips 55, described in more detail with reference to FIGS. 2-5.

Processing circuitry 41 is typically programmed in software in a general purpose microprocessor to transform the general purpose microprocessor into a specific processor and carry out the functions described herein. The software may be downloaded to the computer in electronic form, over a network, for example, or it may, alternatively or additionally, be provided and/or stored on non-transitory tangible media, such as magnetic, optical, or electronic memory.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2A:
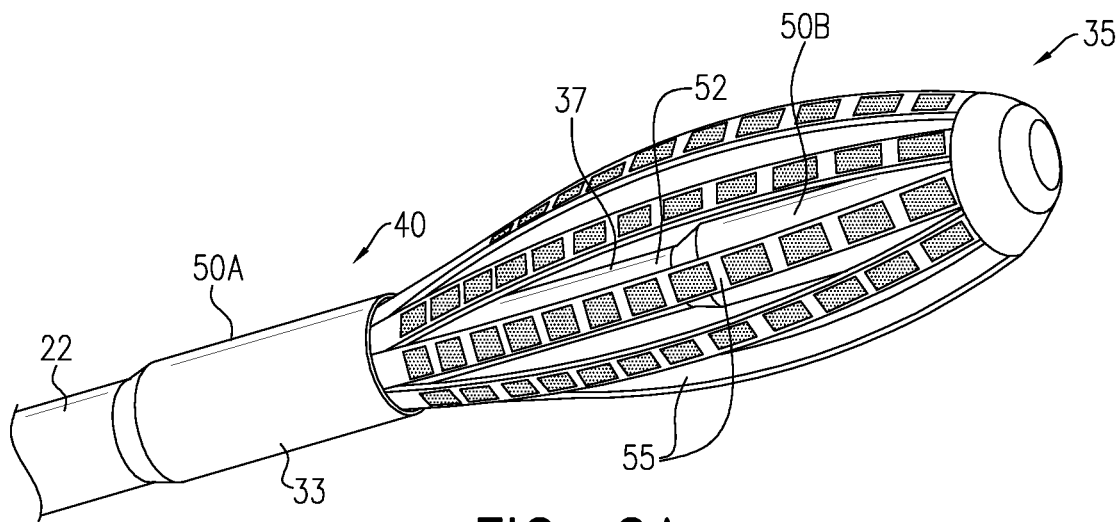
FIG. 2A is a schematic view of a distal end of a basket catheter in a collapsed formation.
Figure 2B:
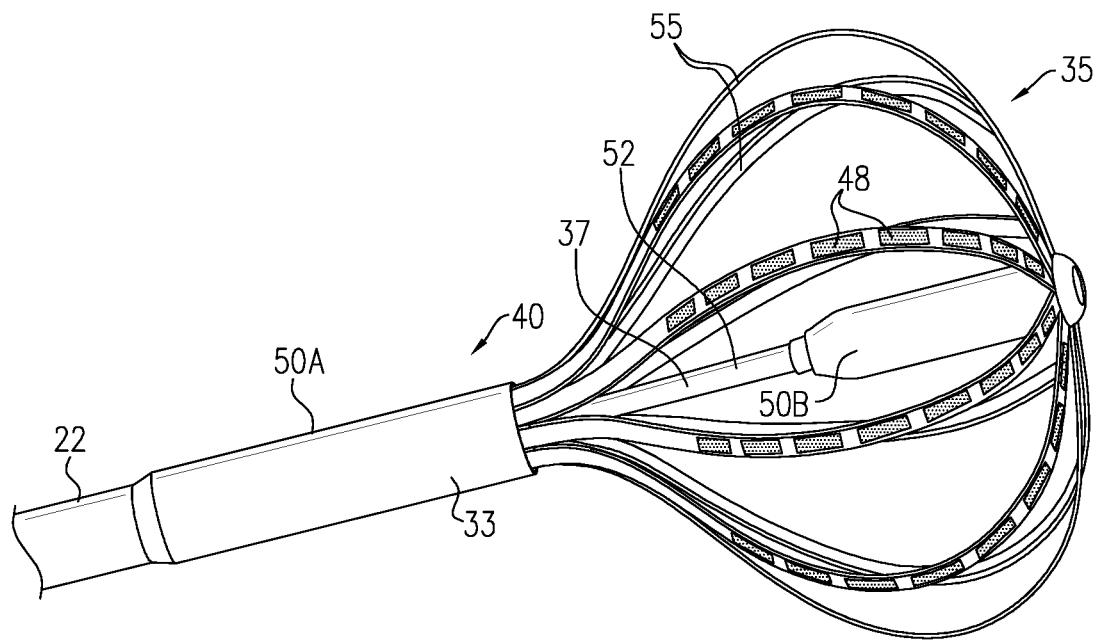
FIG. 2B is a schematic view of the distal end of the basket catheter of FIG. 2A in a deployed formation.

Reference is now made to FIGS. 2A and 2B. FIG. 2A is a schematic view of a distal end of the basket catheter 40 in a collapsed formation. FIG. 2B is a schematic view of the distal end of the basket catheter 40 of FIG. 2A in a deployed formation.

The magnetic sensor 50A is a coil-based position sensor disposed at the distal end 33 of the insertion tube 22, for example, in the coupling member at the distal end 33. The magnetic sensor 50B is a coil-based position sensor disposed on a distal portion 52 of the pusher 37, for example, in a coupling member of the distal portion 52, coupling the distal ends of the flexible strips 55 to pusher 37. The pusher 37 is configured to be advanced and retracted through the insertion tube 22. Each sensor 50A, 50B may be a SAS, DAS or TAS. The sensors 50A, 50B may be the same type of sensor, or different types of sensor. If both of the sensors 50A, 50B are single-axis sensors, the catheter 40 generally includes another position sensor to track a roll of the assembly 35. The magnetic sensors 50A, 50B are configured to output respective first and second position signals in response to the transmitted alternating magnetic fields transmitted by the magnetic field generator coil(s) 42 (FIG. 1).

The assembly 35 is typically an expandable assembly comprising the flexible strips 55 (only some labeled for the sake of simplicity) disposed circumferentially around the distal portion 52 of the pusher 37 with first ends of the strips 55 connected to the distal end 33 (e.g., the coupling member of the distal end 33) of the insertion tube 22 and second ends of the strips 55 connected to the distal portion 52 (e.g., the coupling member of the distal portion 52) of the pusher 37. The flexible strips 55 are configured to bow radially outward when the pusher 37 is retracted. A plurality of the electrodes 48 (only some labeled for the sake of simplicity) are disposed on each of the flexible strips 55.

Figure 3A:
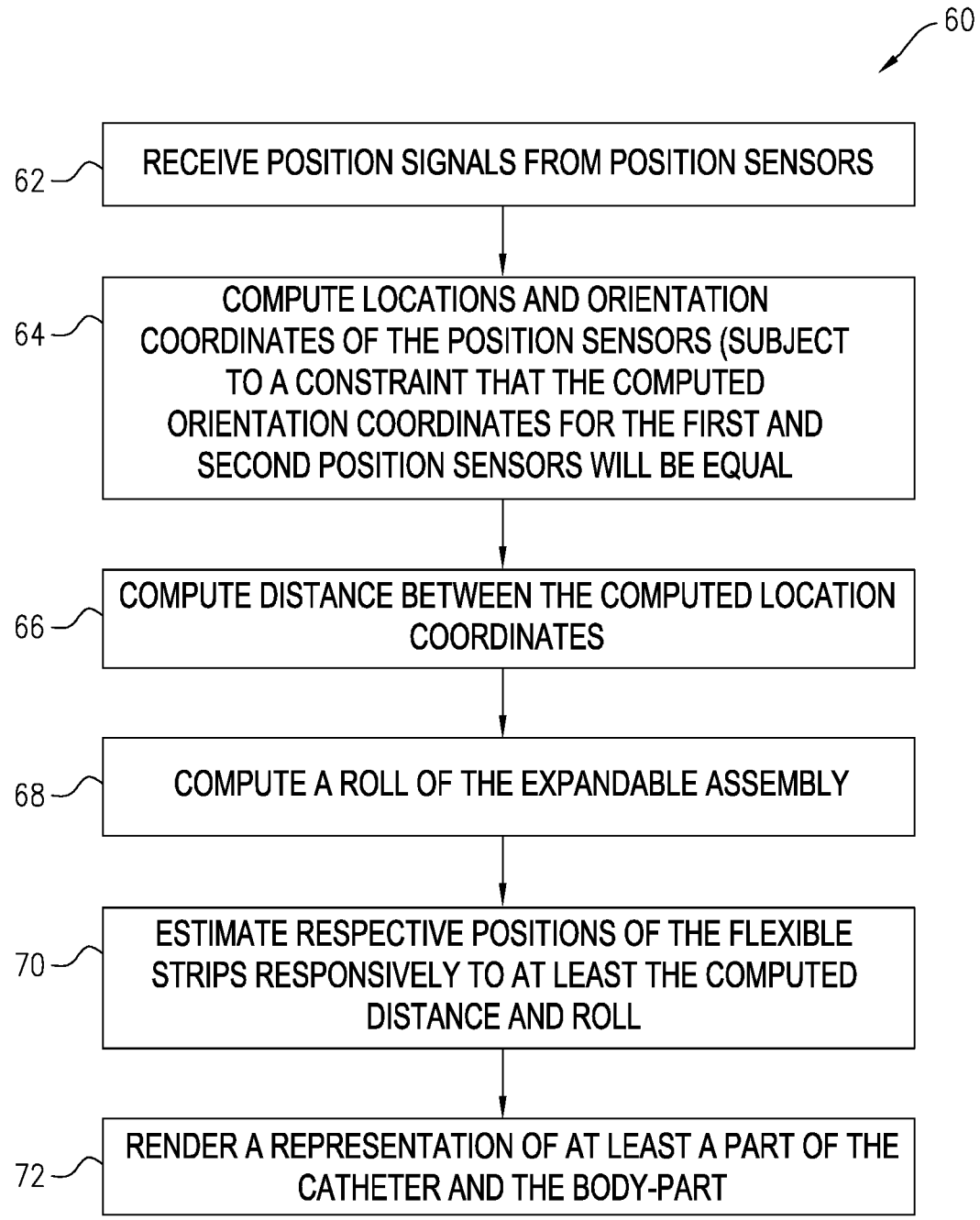
FIG. 3A is a flowchart including steps in a method of operation of the system of FIG. 1 using the basket catheter of FIGS. 2A and B.

Reference is now made to FIG. 3A, which is a flowchart 60 including steps in a method of operation of the system 20 of FIG. 1 using the basket catheter 40 of FIGS. 2A and B.

The processing circuitry 41 (FIG. 1) is configured to receive (block 62) the first and second position signals from the magnetic sensors 50A, 50B, respectively. In some embodiments, the magnetic sensor 50A may provide one or more position signals corresponding to one or more coils of the magnetic sensor 50A. Similarly, the magnetic sensor 50B may provide one or more position signals corresponding to one or more coils of the magnetic sensor 50B.

The processing circuitry 41 is configured to compute (block 64) location and orientation coordinates for the magnetic sensors 50A, 50B based on the received signals, and using a position computation in which the location and orientation coordinates of each of the magnetic sensors 50A, 50B are interdependently computed in an iterative manner responsively to the respective received position signal, and subject to a constraint that the magnetic sensors 50A, 50B (include coils that) are coaxial and therefore have a same orientation.

In some embodiments, the processing circuitry 41 is configured to compute the location and orientation coordinates for the magnetic sensors 50A, 50B subject to a constraint that the computed orientation coordinates for the magnetic sensors 50A, 50B will be equal within a given tolerance, such as plus or minus 2 degrees. The step of block 64 is described in more detail with reference to FIGS. 3B and 3C.

The processing circuitry 41 is configured to compute (block 66) a distance between the computed location coordinates of the magnetic sensor 50A and the computed location coordinates of the magnetic sensor 50B. The computed distance is indicative of the bow of the flexible strips 55 (FIG. 2B) and the general shape of the basket assembly 35 (FIG. 2B) as will be described below in more detail with reference to the step of block 70.

The processing circuitry 41 is configured to compute (block 68) a roll of the expandable assembly 35 responsively to the position signal(s) from the magnetic sensor 50A and/or from the magnetic sensor 50B and/or from another position sensor of the catheter 40. As mentioned previously, the sensor providing data for computation of roll is typically a DAS or TAS.

The bow of the flexible strips 55 and/or the positions of the electrodes 48 (or other features) on the flexible strips 55 with respect to a fixed point on the catheter 40 (such as the distal tip of the insertion tube 22) may be measured for various distances between the magnetic sensors 50A, 50B. For example, the positions of the electrodes 48 with respect to a fixed point on the catheter 40 may be measured for every 0.2 mm movement of the pusher 37 with respect to the insertion tube 22, and after each 0.2 mm movement, the computed distance between the magnetic sensors 50 is recorded along with the positions of the electrodes 48. This data may then be used to find the bow of the flexible strips 55 and/or the positions of the electrodes 48 (or other features) on the flexible strips 55 with respect to a fixed point on the catheter 40 (such as the distal tip of the insertion tube 22) responsively to the computed distance between the magnetic sensors 50.

In some embodiments, the bow of the flexible strips 55 and/or the positions of the electrodes 48 (or other features) on the flexible strips 55 with respect to a fixed point on the catheter 40 (such as the distal tip of the insertion tube 22) may be computed based on the computed distance between the magnetic sensors 50 and a model of the catheter 40 which provides the bow of the flexible strips 55 and/or the positions of the electrodes 48 for the computed distance based on the mechanical properties and dimensions of the flexible strips 55.

The processing circuitry 41 is configured to estimate (block 70) respective positions of the flexible strips 55 responsively to the computed distance, the computed roll and the computed location and orientation coordinates of one or more of the magnetic sensors 50. The computed distance provides the respective positions of the flexible strips 55 with respect to a fixed point of the catheter 40. The computed roll, location and orientation coordinates of one or more of the magnetic sensors 50 provides the respective positions of the flexible strips 55 with respect to a magnetic coordinate frame used in the system 20.

The processing circuitry 41 is configured to render (block 72) to the display 27 (FIG. 1), the representation 31 (FIG. 1) of at least a part of the catheter 40 and the body-part (e.g., the heart 26) responsively to the estimated respective positions of the flexible strips 55 and a computed position of the insertion tube 22 (for example, based on signal(s) received from the magnetic sensor 50A).

Figure 3B:
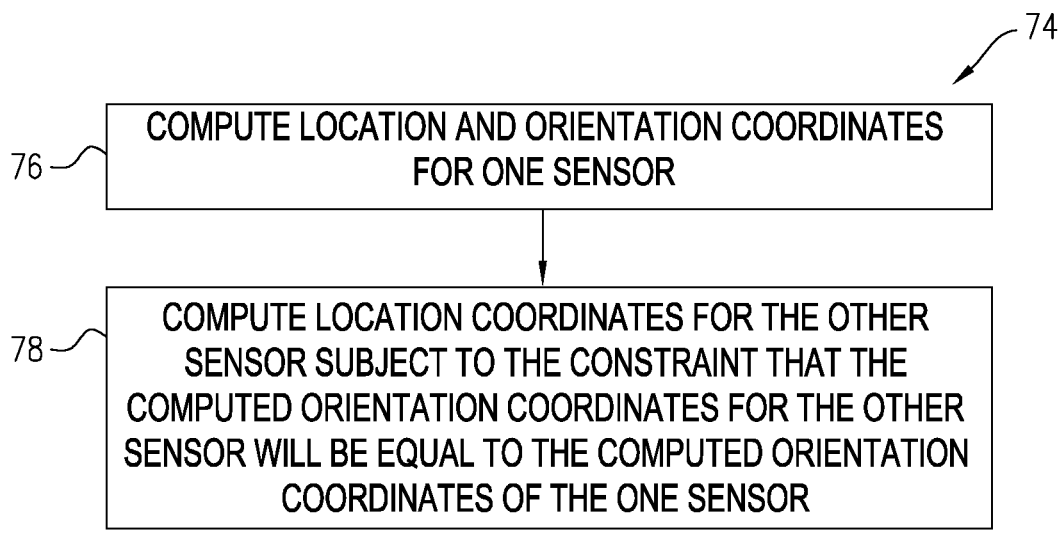
FIG. 3B is a flowchart including sub-steps in the method of operation FIG. 3A.

Reference is now made to FIG. 3B, which is a flowchart 74 including sub-steps in the method of operation FIG. 3A. The following sub-steps are sub-steps of the step of block 64 of FIG. 3A.

The processing circuitry 41 (FIG. 1) is configured to compute (block 76) the location and orientation coordinates for one sensor of the magnetic sensors 50A, 50B using the position computation, responsively to the received signal(s) of the one sensor. The processing circuitry 41 is configured to compute (block 78) the location coordinates for the other sensor of the magnetic sensors 50A, 50B using the position computation, subject to a constraint that the computed orientation coordinates for the other sensor will be equal to the computed orientation coordinates of the one sensor within a given tolerance, such as plus or minus 2 degrees.

Figure 3C:
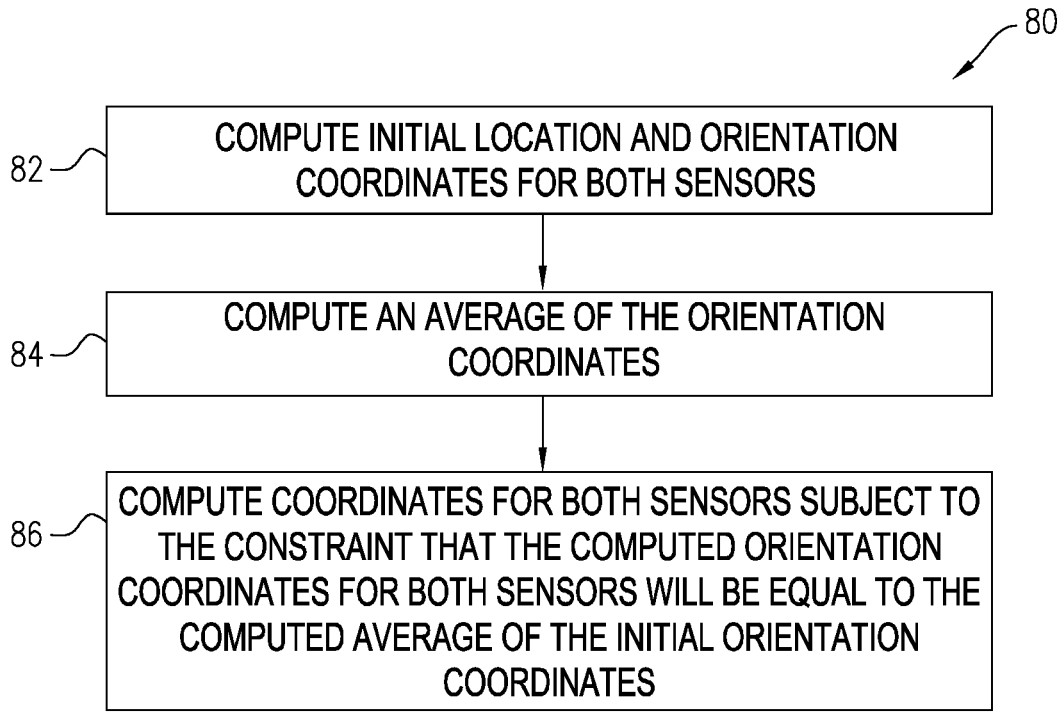
FIG. 3C is a flowchart including alternative sub-steps in the method of operation FIG. 3A.

Reference is now made to FIG. 3C, which is a flowchart 80 including alternative sub-steps in the method of operation FIG. 3A. The following sub-steps are sub-steps of the step of block 64 of FIG. 3A.

The processing circuitry 41 (FIG. 1) is configured to compute (block 82) initial location and initial orientation coordinates for both the magnetic sensors 50 using the position computation.

The processing circuitry 41 is configured to compute (block 84) an average of the initial orientation coordinates of the magnetic sensors 50. For example, if the orientation coordinates are represented by two angles $\theta$, $\varphi$, for example representing yaw and pitch respectively, the orientation of magnetic sensor 50A being $\theta_A$, $\varphi_A$ and the orientation of magnetic sensor 50B being $\theta_B$, $\varphi_B$, the average orientation of the magnetic sensor 50 is equal to the $\theta_{av}$, $\varphi_{av}$, where $\theta_{av}$ is the average of $\theta_A$ and $\theta_B$, and $\varphi_{av}$ is the average of $\varphi_A$ and $\varphi_B$.

The processing circuitry 41 is configured to compute (block 86) the location and orientation coordinates for magnetic sensors 50 using the position computation based on the signals received from the sensors 50 and subject to a constraint that the orientation coordinates for both magnetic sensors 50 will be equal to the computed average of the initial orientation coordinates within a given tolerance, such as plus or minus 2 degrees.

Figure 4A:
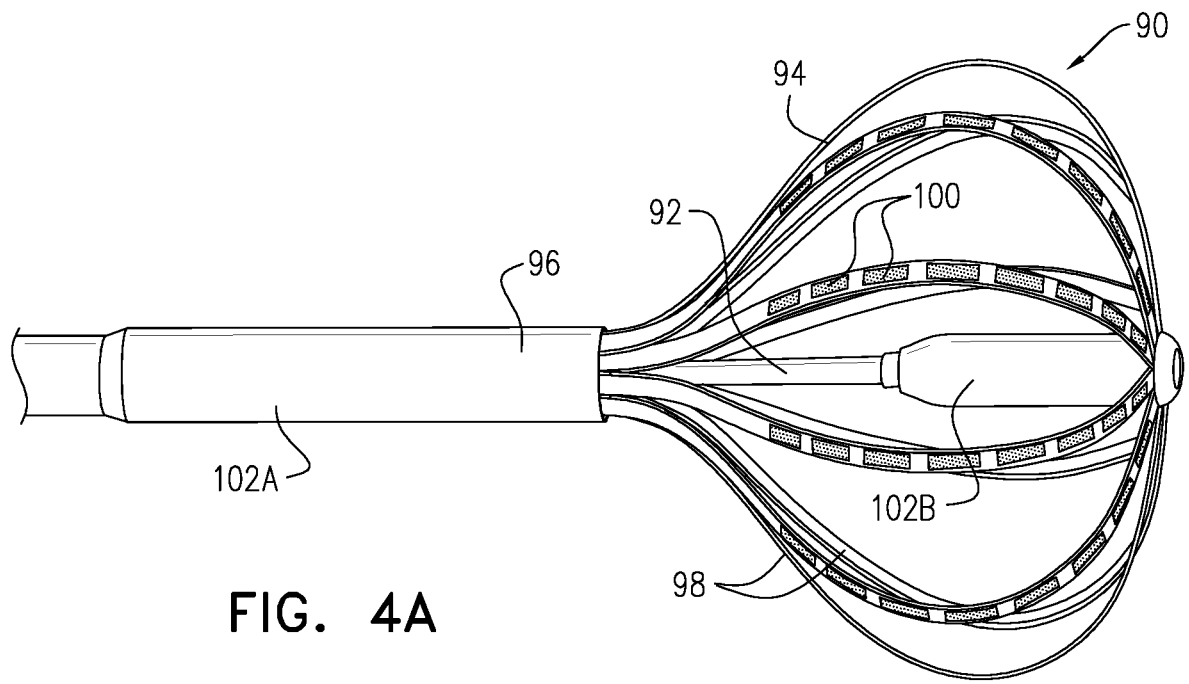
FIG. 4A is a schematic view of a distal end of a basket catheter.
Figure 4B:
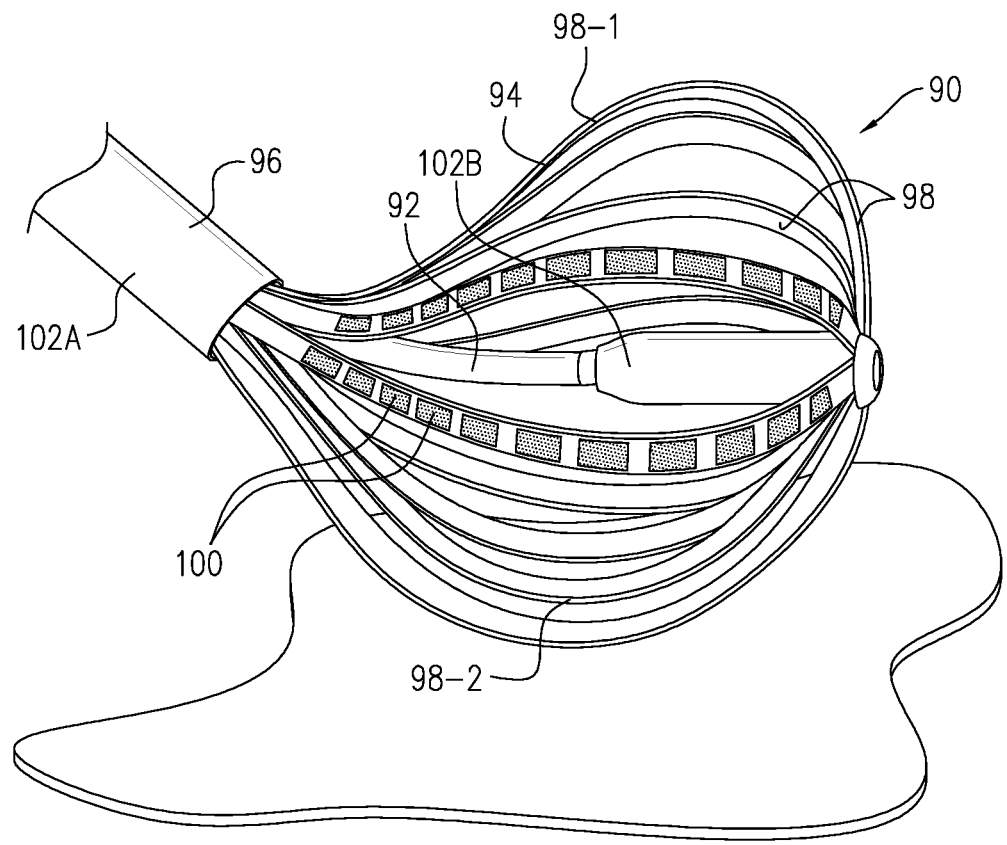
FIG. 4B is a schematic view of the distal end of the basket catheter of FIG. 4A after being deformed to the side.

Reference is now made to FIGS. 4A and 4B. FIG. 4A is a schematic view of a distal end of a basket catheter 90. FIG. 4B is a schematic view of the distal end of the basket catheter 90 of FIG. 4A after being deformed to the side. The basket catheter 90 is substantially the same as the catheter 40 of FIGS. 2A and 2B except that basket catheter 90 includes a pusher 92 and an expandable assembly 94 (e.g., basket) that can be pushed to the side with respect to the axis of an insertion tube 96 of the basket catheter 90. For example, when the expandable assembly 94 is pushed against tissue, the expandable assembly 94 may deform. Similarly, to the catheter 40 of FIG. 2A, the basket catheter 90 includes multiple flexible strips 98 (only some labeled for the sake of simplicity), electrodes 100 (only some labeled for the sake of simplicity) disposed on each of the flexible strips 98, and two magnetic sensors 102A, 102B (similar to the magnetic sensors 50 of FIG. 2A). The magnetic sensor 102A is disposed at the distal end of the insertion tube 96 (e.g., in a coupling member coupling the insertion tube 96 to the assembly 94) and the magnetic sensor 102B is disposed at the distal end of the pusher 92 (e.g., in a coupling member coupling the pusher 92 with distal ends of the flexible strips 98).

FIG. 4B shows that some of the flexible strips 98 are more bowed than others due to the expandable assembly 94 being pushed against tissue. For example, the flexible strip 98-1 is more bowed than the other flexible strips 98. Additionally, some of the flexible strips 98, e.g., the flexible strip 98-2, are less bowed than they would be if the expandable assembly 94 was not pushed against tissue. It can also be clearly seen from FIG. 4B that the magnetic sensors 102 are not coaxial and that the axis of the magnetic sensor 102B is pointing away from the axis of the insertion tube 96 that includes the magnetic sensor 102A.

Figure 5:
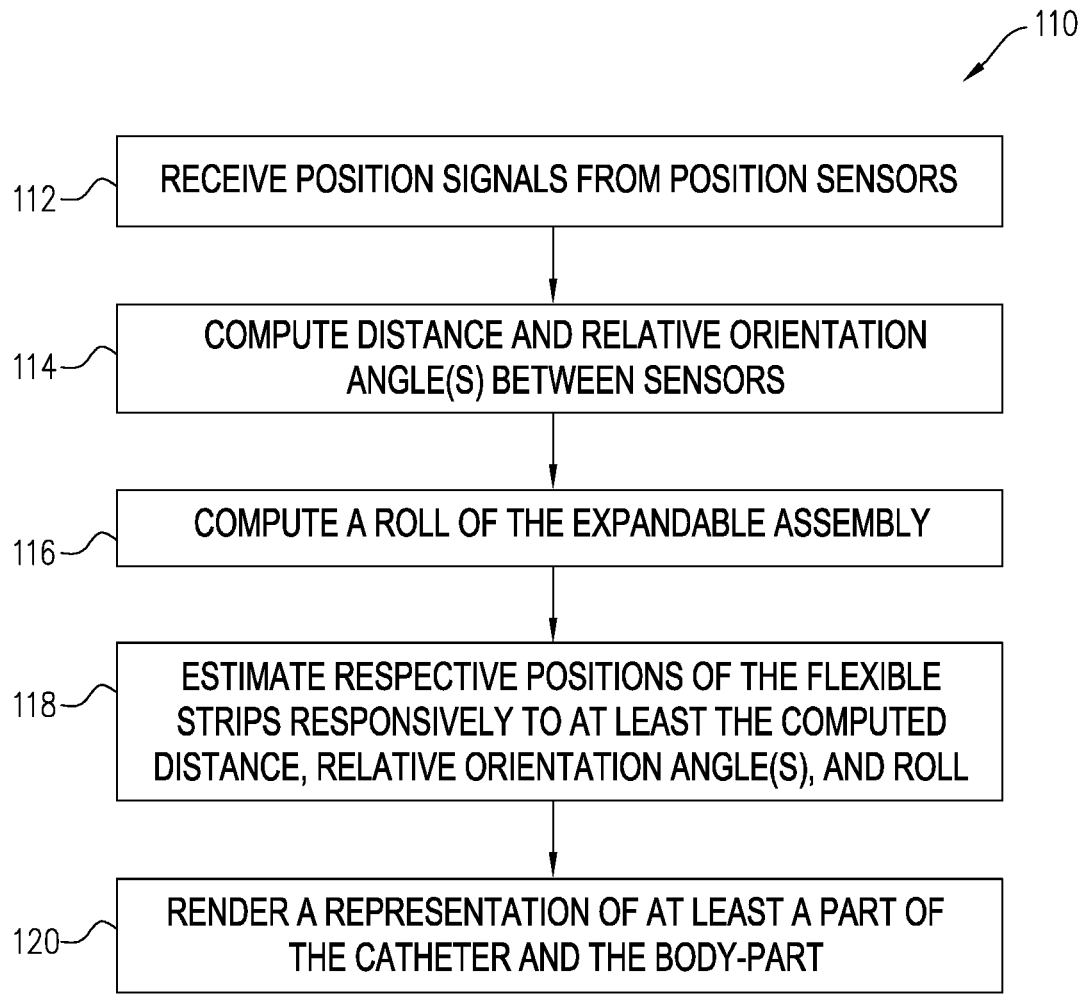
FIG. 5 is a flowchart including steps in a method of operation of the system of FIG. 1 using the basket catheter of FIGS. 4A and B.

Reference is now made to FIG. 5, which is a flowchart 110 including steps in a method of operation of the system 20 of FIG. 1 using the basket catheter 90 of FIGS. 4A and B. Reference is also made to FIGS. 4A and 4B.

The processing circuitry 41 (FIG. 1) is configured to receive (block 112) first and second position signals from the magnetic sensors 102A, 102B, respectively. In some embodiments, the magnetic sensor 102A may provide one or more position signals corresponding to one or more coils of the magnetic sensor 102A. Similarly, the magnetic sensor 102B may provide one or more position signals corresponding to one or more coils of the magnetic sensor 102B.

The processing circuitry 41 is configured to compute (block 114) a distance and a relative orientation angle between the magnetic sensors 102 responsively to the received position signals. The relative orientation angle having a value greater than zero is generally indicative that the expandable assembly 94 is deflected to a side with respect to an axis of the insertion tube 96, and that at least some of the flexible strips 98 are distorted as compared to a shape of the flexible strips 98 when the expandable assembly 94 is centrally positioned around the axis of the insertion tube 96.

The processing circuitry 41 is configured to compute (block 116) a roll of the expandable assembly 94 responsively to the position signal(s) from one or more of the magnetic sensors 102 or from another sensor disposed on the basket catheter 90.

The bow of the flexible strips 98 and/or the positions of the electrodes 100 (or other features) on the flexible strips 98 with respect to a fixed point on the catheter 90 (such as the distal tip of the insertion tube 96) may be measured for various distances between the magnetic sensors 102 and for various relative orientation angles between the magnetic sensors 102. For example, the positions of the electrodes 100 with respect to the fixed point on the catheter 90 may be measured for approximately every 0.2 mm movement of the pusher 92 with respect to the insertion tube 96 and for every 1 degree of relative orientation between the magnetic sensors 102 (up to a maximum sideways movement of the expandable assembly 94). At each different distance/relative-orientation combination, the computed distance and computed relative orientation angle between the magnetic sensors 50 is recorded along with the position data of the electrodes 100. This data may then be used to estimate the bow of the flexible strips 98 and/or the positions of the electrodes 100 (or other features) on the flexible strips 100 with respect to a fixed point on the catheter 90 (such as the distal tip of the insertion tube 96) responsively to the computed distance and relative orientation angle between the magnetic sensors 102.

Additionally, or alternatively, the bow of the flexible strips 98 may be estimated based on the following assumptions: (a) each of the flexible strips 98 is of a fixed and known length; (b) each of the flexible strips 98 is connected to the coupling member, which couples the pusher 92 with the distal ends of the flexible strips 98, substantially perpendicular (within an error of plus or minus 10 degrees) to a longitudinal axis of that coupling member; (c) each of the flexible strips 98 is connected to the coupling member, which couples the proximal ends of the flexible strips 98 to the insertion tube 96, substantially parallel (within an error of plus or minus 10 degrees) to the longitudinal axis of the insertion tube 96. Based on the above assumptions (a)-(c), and the computed positions of the coupling members based on the computed positions of the magnetic sensors 102, the bow of each of the flexible strips 98 may be computed using a third-degree polynomial. In some embodiments, the bow of the flexible strips 98 and/or the positions of the electrodes 100 (or other features) on the flexible strips 98 with respect to a fixed point on the catheter 90 (such as the distal tip of the insertion tube 96) may be computed based on the computed distance and orientation between the magnetic sensors 102 and a model of the catheter 90 which provides the bow of the flexible strips 98 and/or the positions of the electrodes 100 for the computed distance based on the mechanical properties and dimensions of the flexible strips 98.

The processing circuitry 41 is configured to estimate (block 118) respective positions of the flexible strips 98 responsively to at least the computed distance and relative orientation angle, while accounting for a distortion of one or more of the flexible strips 98 from a symmetrical disposition when the relative orientation angle has a value greater than zero. The computed distance and relative orientation angle between the magnetic sensors 102 provide the respective positions of the flexible strips 98 with respect to a fixed point of the catheter 90. The computed roll, location and orientation coordinates of one or more of the magnetic sensors 102 provides the respective positions of the flexible strips 98 with respect to the magnetic coordinate frame used in the system 20.

The processing circuitry 41 is configured to render (block 120) to the display 27 (FIG. 1), the representation 31 (FIG. 1) of at least a part of the catheter 90 and the body-part (e.g., the heart 26) responsively to the estimated respective positions of the flexible strips 98 and a computed position of the insertion tube 96 (for example, based on signal(s) received from the magnetic sensor 102A).

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:
1. A system comprising:
 a catheter configured to be inserted into a body-part of a living subject, and comprising:
  an insertion tube including a distal end, and a first coil-based position sensor disposed at the distal end;
  a pusher including a second coil-based position sensor disposed thereon and a distal portion, and being configured to be advanced and retracted through the insertion tube; and an expandable assembly comprising a plurality of flexible strips disposed circumferentially around the distal portion of the pusher, with first ends of the flexible strips connected to the distal end of the insertion tube and second ends of the flexible strips connected to the distal portion of the pusher, the flexible strips being configured to bow radially outward when the pusher is retracted;

at least one magnetic field radiator configured to transmit alternating magnetic fields into a region where the body-part is located, the first and second coil-based position sensors being configured to output respective first and second position signals in response to the transmitted alternating magnetic fields; and processing circuitry configured to:
receive the first and second position signals from the first and second coil-based position sensors;
compute a distance and a relative orientation angle between the first and second coil-based position sensors responsively to the received first and second position signals; and
estimate respective positions of the flexible strips responsively to at least the computed distance and relative orientation angle, while accounting for a distortion of one or more of the flexible strips from a symmetrical disposition when the relative orientation angle has a value greater than zero.

2. The system according to claim 1, wherein the processing circuitry is configured to compute a roll of the expandable assembly responsively to the position signal from at least one of the first or second coil-based position sensors.

3. The system according to claim 2, further comprising a display, wherein the processing circuitry is configured to render to the display a representation of at least a part of the catheter and the body-part responsively to the estimated respective positions of the flexible strips.

4. The system according to claim 1, wherein the processing circuitry is configured to:
compute the location and orientation coordinates for one sensor of the first and second coil-based position sensors using the position computation; and
compute the location coordinates for another sensor of the first and second coil-based position sensors subject to a constraint that the computed orientation coordinates for the other sensor will be equal to the computed orientation coordinates of the one sensor within a given tolerance.

5. The system according to claim 4, wherein the given tolerance is approximately plus or minus two degrees.

6. The system according to claim 1, wherein the processing circuitry is configured to:
compute initial location and initial orientation coordinates for the first and second coil-based position sensors using the position computation;
compute an average of the initial orientation coordinates of the first and second coil-based position sensors; and
compute the location and orientation coordinates for the first and second coil-based position sensors using the position computation subject to a constraint that the orientation coordinates for the first and second coil-based position sensors will be equal to the computed average of the initial orientation coordinates with a given tolerance.

7. The system according to claim 1, wherein the processing circuitry is configured to compute the location and orientation coordinates for the first and second coil-based position sensors subject to a constraint that the computed orientation coordinates for the first and second coil-based position sensors will be equal within a given tolerance.

8. The system according to claim 1, wherein at least one of the first and second coil-based position sensors comprises a dual-axis position sensor.

9. The system according to claim 1, wherein at least one of the first coil-based position sensor comprises a triple-axis position sensor.

10. The system according to claim 1, wherein the first and second coil-based position sensors are coaxial.

11. The system according to claim 1, wherein the plurality of flexible strips comprises a plurality of electrodes.

12. The system according to claim 11, wherein at least some of the electrodes of the plurality of electrodes are configured to detect electrophysiological signals for electro-anatomical mapping.

13. The system according to claim 11, wherein at least some of the electrodes of the plurality of electrodes are configured to deliver ablative energy to tissue.

14. A method, comprising:
inserting a catheter into a body-part of a living subject, the catheter comprising an insertion tube, a first coil-based position sensor disposed at a distal end of the insertion tube, a pusher including a second coil-based position sensor disposed thereon, an expandable assembly including flexible strips disposed circumferentially around a distal portion of the pusher, with first ends of the strips connected to the distal end of the insertion tube and second ends of the strips connected to the distal portion of the pusher;
retracting the pusher causing the flexible strips to bow radially outward;
transmitting alternating magnetic fields into a region where the body-part is located;
outputting by the first and second coil-based position sensors respective first and second position signals in response to the transmitted alternating magnetic fields;
receiving the first and second position signals from the first and second coil based position sensors;
computing a distance and a relative orientation angle between the first and second coil-based position sensors responsively to the received first and second position signals; and
estimating respective positions of the flexible strips responsively to at least the computed distance and relative orientation angle, while accounting for a distortion of one or more of the flexible strips from a symmetrical disposition when the relative orientation angle has a value greater than zero.

15. The method according to claim 14, further comprising:
computing a roll of the expandable assembly responsively to the position signal from at least one of the first or second coil-based position sensors; and
rendering to a display a representation of at least a part of the catheter and the body-part responsively to the estimated respective positions of the flexible strips.

16. The method according to claim 14, further comprising:
computing the location and orientation coordinates for one sensor of the first and second coil-based position sensors using the position computation; and
computing the location coordinates for another sensor of the first and second coil-based position sensors subject to a constraint that the computed orientation coordinates for the other sensor will be equal to the computed orientation coordinates of the one sensor within a given tolerance.

17. The method according to claim 14, further comprising:
    computing initial location and initial orientation coordinates for the first and second coil-based position sensors using the position computation;
    computing an average of the initial orientation coordinates of the first and second coil-based position sensors; and
    computing the location and orientation coordinates for the first and second coil-based position sensors using the position computation subject to a constraint that the orientation coordinates for the first and second coil-based position sensors will be equal to the computed average of the initial orientation coordinates with a given tolerance.

18. The method according to claim 14, further comprising computing the location and orientation coordinates for the first and second coil-based position sensors subject to a constraint that the computed orientation coordinates for the first and second coil-based position sensors will be equal within a given tolerance.

19. The method according to claim 14, wherein the first and second coil-based position sensors are coaxial.

20. The method according to claim 14, wherein the flexible strips comprises a plurality of electrodes.

* * * * *